United States Patent
Choi et al.

(10) Patent No.: US 9,636,027 B2
(45) Date of Patent: May 2, 2017

(54) ULTRASENSITIVE AND COMPACT DEVICE FOR NONINVASIVE ACQUISITION OF LOW STRENGTH BIO SIGNALS AND METHOD OF USING SAME

(71) Applicant: JINGA-HI, INC., Sunnyvale, CA (US)

(72) Inventors: Mee H. Choi, Sunnyvale, CA (US); Lu Xu, San Pablo, CA (US)

(73) Assignee: JINGA-HI, INC., Sunnyvale, CA (US)

( * ) Notice: Subject to any disclaimer, the term of this patent is extended or adjusted under 35 U.S.C. 154(b) by 689 days.

(21) Appl. No.: 13/912,900

(22) Filed: Jun. 7, 2013

(65) Prior Publication Data
US 2014/0364759 A1    Dec. 11, 2014

Related U.S. Application Data

(60) Provisional application No. 61/660,529, filed on Jun. 15, 2012.

(51) Int. Cl.
| | |
|---|---|
| *A61B 5/05* | (2006.01) |
| *A61B 5/04* | (2006.01) |
| *A61B 5/0476* | (2006.01) |
| *A61B 5/00* | (2006.01) |

(52) U.S. Cl.
CPC ........ *A61B 5/04001* (2013.01); *A61B 5/0476* (2013.01); *A61B 5/7225* (2013.01); *A61B 5/0006* (2013.01)

(58) Field of Classification Search
CPC ................ A61B 5/0476; A61B 5/04
See application file for complete search history.

(56) References Cited

U.S. PATENT DOCUMENTS

| | | |
|---|---|---|
| 7,420,366 B1 | 9/2008 | In et al. |
| 7,528,606 B1 | 5/2009 | In et al. |
| 7,714,671 B1 | 5/2010 | In et al. |
| 7,777,535 B1 | 8/2010 | In et al. |
| 7,902,931 B1 | 3/2011 | In et al. |
| 8,049,486 B1 | 11/2011 | In et al. |
| 8,049,570 B1 | 11/2011 | In et al. |
| 8,165,557 B1 | 4/2012 | In et al. |
| 8,174,325 B1 | 5/2012 | Leung et al. |
| 8,207,763 B1 | 6/2012 | In et al. |
| 8,212,569 B1 | 7/2012 | In et al. |
| 2007/0161919 A1* | 7/2007 | DiLorenzo ......... A61B 5/04001 600/544 |
| 2008/0269630 A1* | 10/2008 | Denison ............... A61B 5/0478 600/544 |

\* cited by examiner

*Primary Examiner* — Christian Jang
(74) *Attorney, Agent, or Firm* — Innovation Counsel LLP

(57) ABSTRACT

A method of detecting changes in biologically sourced electrical signals is disclosed. Biologically sourced electrical signals are coupled to a meta-stable and hair-trigger wise perturbable system. The system operates in a first oscillatory mode when the received signals have a strength below a first predetermined level and operates in a distinguishable second oscillatory mode when the received signals have strengths above the first predetermined level but below a second predetermined level. The strengths of the received and thusly distinguishable signals may be in a range below 10 picoAmperes. The biologically sourced electrical signals may be driven by intracranial nerve firings.

9 Claims, 14 Drawing Sheets

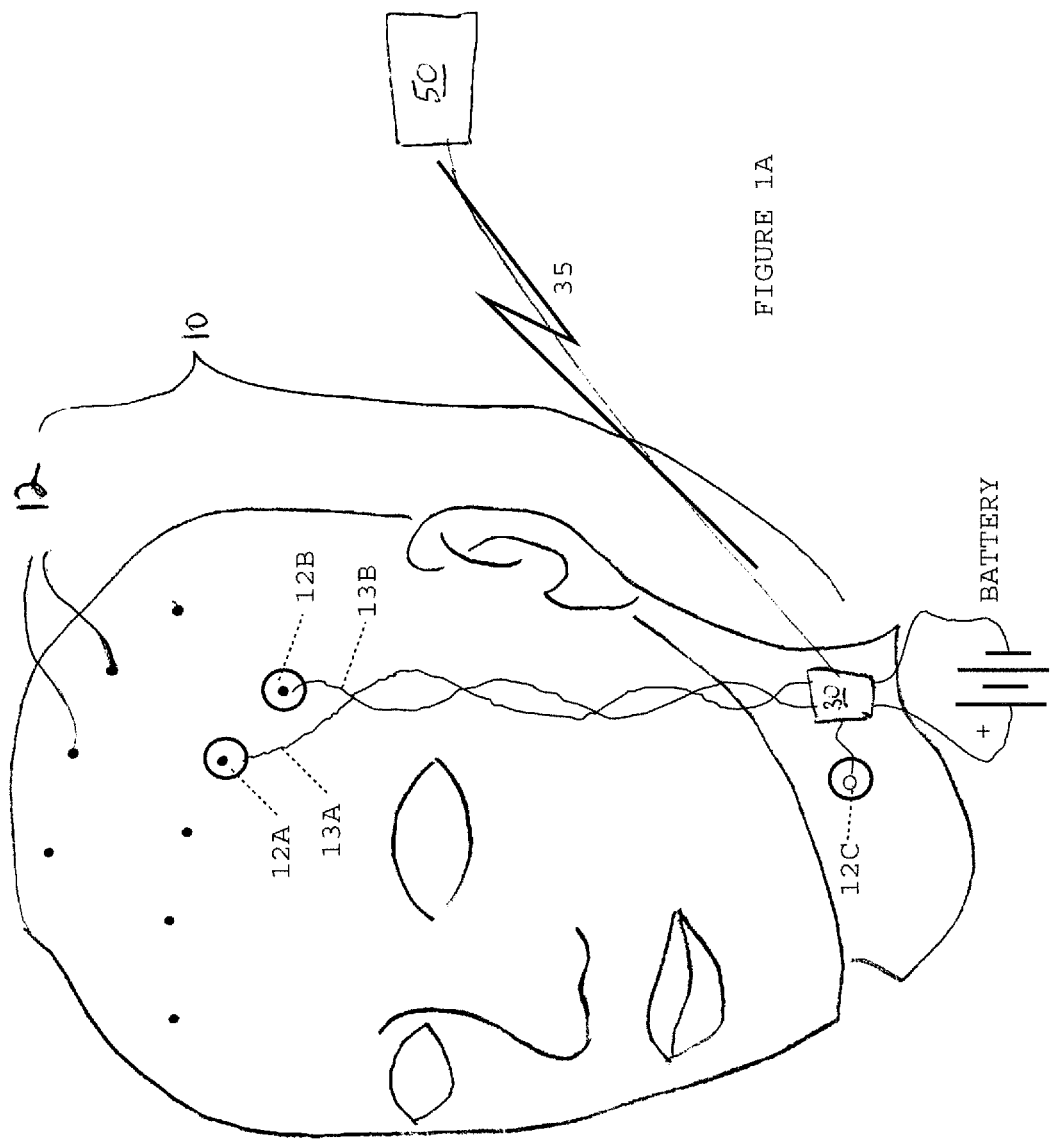

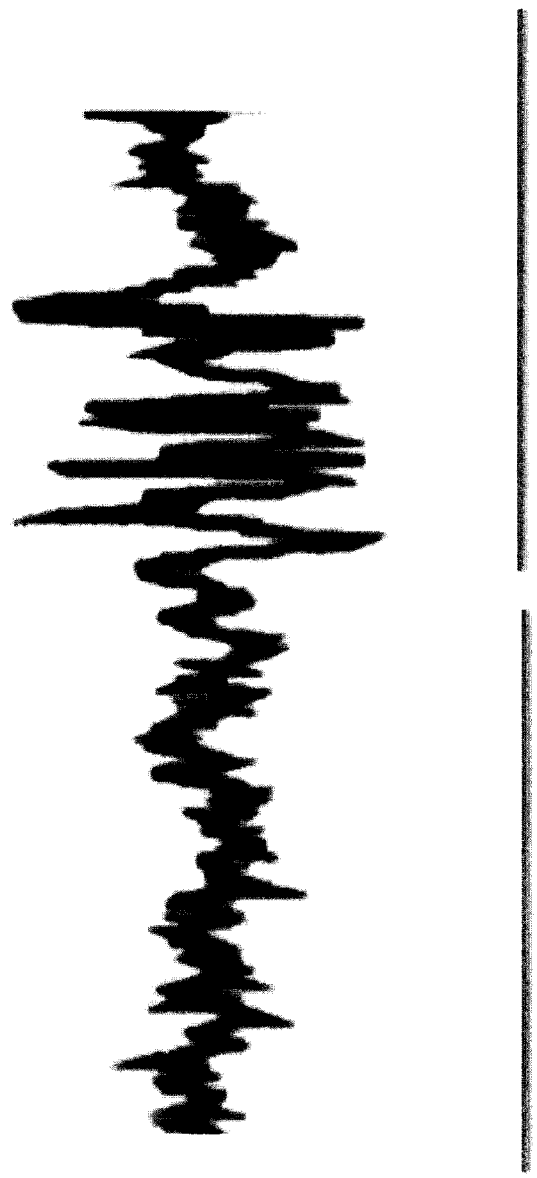

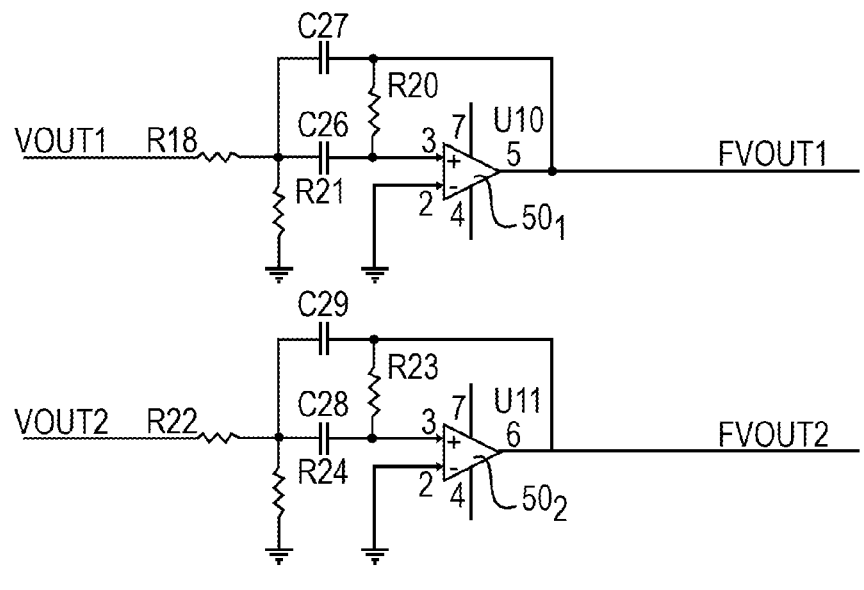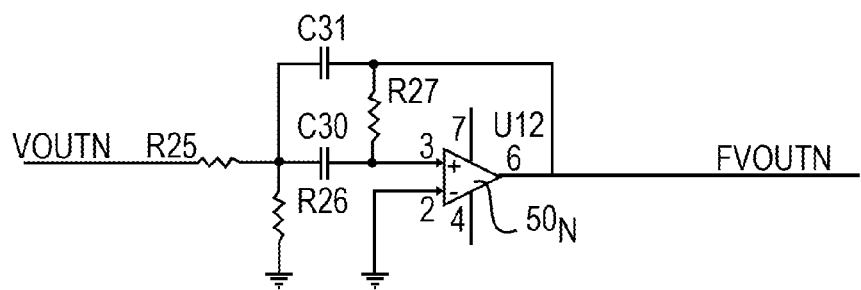
FIG. 5

ULTRASENSITIVE AND COMPACT DEVICE FOR NONINVASIVE ACQUISITION OF LOW STRENGTH BIO SIGNALS AND METHOD OF USING SAME

REFERENCE TO RELATED APPLICATIONS

The present application claims benefit of and is a continuation-in-part of U.S. Provisional application Ser. No. 61/660,529 filed Jun. 15, 2012 by Mee H. Choi and Lu Xu and entitled High Fidelity Biopotential Measurement Device, where the disclosure of said Provisional application is incorporated herein by reference in its entirety.

REFERENCE TO RELATED PATENTS

The disclosures of the following identified patents (A)-(K) are further incorporated herein by reference:

(A) U.S. Pat. No. 8,049,570 "Coupled Bi-Stable Microcircuit System for Ultra-Sensitive Electrical and Magnetic Field Sensing";

(B) U.S. Pat. No. 8,212,569 "Coupled Bi-Stable Circuit for Ultra-Sensitive Electric Field Sensing Utilizing Differential Transistors Pairs";

(C) U.S. Pat. No. 7,714,671 "Wideband nonlinear 'channelizer' for rapid processing of static and timeperiodic signals";

(D) U.S. Pat. No. 7,777,535 "Coupled Nonlinear Elements for Frequency Down-Conversion Systems and Methods";

(E) U.S. Pat. No. 8,165,557 "Frequency Down-Conversion Systems Using Arrays of Coupled Nonlinear Dynamic Elements";

(F) U.S. Pat. No. 7,902,931 "Wideband Non-Linear Circuits for Implementation in Frequency Channel Separation";

(G) U.S. Pat. No. 8,207,763 "Nonlinear Channelizer Device With Wideband, High-Frequency Operation and Channel Reconfigurability";

(H) U.S. Pat. No. 8,174,325 "Adaptive injection locked oscillator array for broadband spectrum RF analysis";

(I) U.S. Pat. No. 7,420,366 "Coupled Nonlinear Sensor System";

(J) U.S. Pat. No. 7,528,606 "Coupled Non-linear Sensor System for Sensing a Time-dependent Target Signal and Method of Assembling the System"; and (K) U.S. Pat. No. 8,049,486 "Coupled electric field sensors for DC target electric field detection".

FIELD OF DISCLOSURE

The present disclosure of invention relates to noninvasive acquisition of low strength biological signals and more specifically to detection of changes in neuronal activity in animal (e.g., mammalian) systems including noninvasive detection of changes in neuronal activity for example of the human brain. The disclosure is more specifically directed to use of hair-triggered nonlinear sensor systems wherein a small change of input for example from a biologically-sourced signal (voltage and/or current) causes a substantially larger and nonlinear change of behavior in a hair-triggered-type of tippable system; for example in a feedback connected circuit comprised of a number of nonlinear stages connected to each other in a feedback loop, where that circuit will meta-stably sustain a first set of critically damped intrinsic oscillations of a predetermined frequency and/or of predetermined output waveforms when in a predetermined critical, meta-stabilized mode (having corresponding critical parameters) but will be nonlinearly perturbed far away from that meta-stable state into a clearly distinguishable alternate state (e.g., different frequencies, different waveforms) when subjected to incoming biological signals of certain magnitudes and/or frequencies even where the biological signals (e.g., neuronally driven signals) are of relatively weak strength (e.g., less than 10 picoamps {pA} in AC strength for example).

BACKGROUND

Animal nerve systems (including those that drive muscular and cardiac functions), and more particularly those of relatively complex living creatures such a mammals and yet more specifically, of humans; can contain thousands of nerve cells packed closely together and firing in various ways (e.g., frequencies, strengths, concurrencies, mutual exclusivities, etc.) depending on underlying states of the corresponding nervous system. Such activities can be monitored in vivo invasively by penetrating through skin and/or skull and electrically (or electro-optically) coupling directly to individual nerve cells. However, such invasive techniques have their drawbacks, particularly in cases where the subject is relatively healthy and invasive procedure is not otherwise called for.

Invasive determination of neuronal activity often entails use of linear bio-current detecting or linear bio-potential detecting devices respectively having a linear and highly sensitive current amplifier or a linear and highly sensitive voltage amplifier, sometimes in respective combination with a linear current-to-voltage converter or a linear voltage-to-current converter. The linear signal inputting device of such methods is typically connected by way of relatively long wires to corresponding probes or electrodes that make contact with the biological specimen under study. For example, in conventional, current-based electrophysiology setups, a biocompatible conducting electrode (e.g., silver, silver chloride, tungsten, or stainless steel) is placed near to a group of neurons or directly inserted into a specific nerve cell. Often, glass pipettes containing the conducting electrode material are inserted inside the neurons. The electrode is electrically coupled by way of a conducting wire to a head input stage of the electrical detection system (for example for linear signal pre-amplification and/or for linear impedance transformation such as from high impedance (e.g., >1K ohm) to low impedance). The head input stage then drives a high-fidelity and linear operational amplifier (for example a circuit having field effect transistors (FET) operating in the linear portions of their IN characteristics). Such high-fidelity and linear input devices tend to be expensive, bulky in size and difficult to integrate into the form of monolithic integrated circuits (IC's). After the received signal is amplified via the front-end high-fidelity and linear input amplifier, various analog signal filtering processes may take place, followed by optional conversion to digital format and further processing by data processing units for example by application to customized spike-sorting algorithms so as to identify meaningful ones among the many neural events that generally take place in the Animal System Under Study (ASUS).

By way of another example, in conventional, voltage-based electrophysiology measurement setups, electrical potential is measured as between two spaced apart points of the animal system under study (ASUS) with one electrode sensing potentials at a predetermined point of interest while the other serves as a reference point (e.g., a reference ground). In this conventional amplification configuration of linearly detecting differential voltages, the meaningful signal that one can detect typically must be at least 10 μV RMS if not more in strength and with a bandwidth in the low kHz range. Due to this limit on conventional electrophysiology, weaker signals below the 10 μV RMS minimum range can only be acquired by use of extensive signal averaging techniques. Even with such extensive signal averaging, it is challenging to identify significant neural events (firings of isolated single cells, or of specific groups of nerve cells or changes in global brainwave activity) because the averaging process tends to bury the significant neural events within the encompassing average of all events. Accordingly, the signals of interest are often lost and cannot be usefully studied or applied for associated purposes.

In academic neuroscience studies, one often follows a laborious process of puncturing cells (patch recording) in order to obtain low-level signals from individual neurons. This procedure usually does not maintain the health of the cells for a long time, nor can it be scaled up for high-throughput drug or other health screening programs. Efforts that were made to reduce the noise introduced by the electronics entail extreme measures such as super cooling of the pre-amplifier stage. Measuring neuronal signals in the brain without puncturing the cells, and attempts at measuring extra-cellular signals result in a lot of noise. Signals below the 1 μV range measured with high-input-resistance electrodes (~1 MΩ or greater) sometimes sink into the noise floor and require extensive signal averaging to overcome noise problems. But then the averaging process itself buries the signal of interest. In addition, when measuring neuronal activities in vivo in intact neurons by placing the electrode near a neuron, the environmental noise tends to be even larger than that experienced for an in vitro lab situation.

Some commercially available electrophysiology machines or multi-electrode arrays (MEA) may be used for drug discovery research. However, while these machines allow measurements to be taken without puncturing the cells and the number of cells easily scale up, they are difficult to use because growing primary neurons in an artificial setting is difficult, and the sensitivity (the signal-to-noise ratio) of these devices is not optimal for characterizing and distinguishing individual neurons. Also, the secondary current effects from the metal surfaces not directly from cells can often create interference. Finally, these devices are extremely bulky, making it difficult to design flexible experiments that can be conveniently carried out by patients (or other subjects, e.g., animal study subjects) of a corresponding clinical trial.

For physician's use, while nearly 100 million people are affected by a brain or nervous system disorder in the United States alone, the devices physicians generally use for dealing with the various disorders suffer from various limitations. For example, current electrophysiology or electroencephalogram (EEG) systems for clinical and surgical (intra-operative) applications are still noisy. Monitoring patients based on evoked potentials (around 10 μV) from an intra-operative EEG requires extensive signal averaging. Furthermore, current hospital and ambulatory EEG devices require wet electrodes, which are not always convenient to use. Although portable EEG devices that utilize dry electrodes may be available, they do not yield any better signal-to-noise ratio than the widely used EEG devices with their wet electrodes. Moreover, long-term monitoring EEG devices used by hospitals tend to be bulky. More critically, there is currently no high fidelity, noninvasive EEG device that can predict abnormal nervous system events from current events and thus provide long-term diagnostic functions.

Factors such as lower signal quality, bulkiness and higher power consumption can hinder designing more flexible experiments for animals or human subjects. Thus, a compact device that yields substantially higher signal-to-noise ratio of neural events that can be measured non-invasively and with low power consumption would play a tremendous role in moving forward the field of neuroscience/neuromedicine. This concept can be further extended to electrophysiology, electroencephalogram, cardiology, and/or electromyography systems.

It is to be understood that this background of the technology section is intended to provide useful background for understanding the here disclosed technology and as such, the technology background section may include ideas, concepts or recognitions that were not part of what was known or appreciated by those skilled in the pertinent art prior to corresponding invention dates of subject matter disclosed herein.

SUMMARY

In accordance with one aspect of the present disclosure, it is recognized that nerve firings are each an all or nothing discrete event. Either a nerve cell fires at its output end (the axon) or it does not. Therefore an ability to "linearly" detect a full range of theoretically possible signal levels with extreme high fidelity is wasteful for the case of nerve behavior studies because what is really needed is a way of detecting whether or not (and when) the nerve fired. What is really needed is a way of detecting weak electromagnetic signals induced by the firing of the under-study nerve cell or group of nerve cells even when the subject (ASUS) is in an environment that contains substantial amounts of ambient electromagnetic noise.

Without wishing to be bound to any specific theory, it is believed that when one or a small cluster of nerves fire, their respective action potential(s) can induce alternating current (AC) micro-currents in the vicinity of the corresponding axon terminal. Some of these AC micro-currents can; depending on local physiology, make their way out to the skin of the mammal (or another creature with a nervous system) as corresponding electromagnetic signaling but at relatively low signal levels, perhaps as micro-currents with strengths in the range of 50 picoamperes (pA) or less, or even as low as 10 pA or less, or more so; even as low as 1-5 pA or less and at various frequencies that are not otherwise absorbed or reflected by intervening tissue.

The present disclosure provides for the use of an ultra-sensitive micro-signal (e.g., micro-current) detecting device which capable of detecting, for example differential alternating current (AC) current changes in the range of 50 picoamperes (pA) or less, or even as low as 10 pA or less, or more so; even as low as 1-5 pA or less. In one embodiment, a meta-stable amplification and feedback system is provided in which a plurality of nonlinear amplifier sensor stages (at least some of which are receiving part of a to be-sensed, micro-signal) are coupled one to the next in a loop to form an oscillator that oscillates in a first and easily-escaped meta-stable mode when no sensor input signal (0 pA) is received but that switches into different and clearly distinguishable, other oscillatory or nonoscillatory modes as the sensor input signal increases by extremely small increments (e.g., in 1 pA increments in the case of detectable micro-currents as an example). The distinguishable modes are detected and mapped (for example by way of digital signal processing) back to the input signal levels (e.g., 1 pA increments) associated with them to thereby determine the input levels that were present and caused corresponding change of modes in the meta-stable amplification and feedback system.

In one embodiment, one or more sets of such closed-loop sensor stages are provided within a monolithically integrated circuit (IC) that is packaged to include or to be directly coupled to biocompatible electrodes such as those picking up pico-Ampere level and alternating current (AC) differential currents for acquisition and local detection by the sensor stages containing IC. By placing just the local detection and amplification IC (and optionally a little more in the way of battery and/or other support circuitry) in close proximity with the subject nervous system for thereby picking up the pico-Ampere level differential currents from close-by sampling points without the need for long probe wires, external signal interference can be reduced. At the same time the local detection and amplification IC (and optionally its local support circuitry, kept at relatively low weight and small size) can be worn (e.g., adhesively carried) by the subject (ASUS) with little discomfort or inconvenience while a remainder of signal processing is carried out in a downstream signal processing device that is wirelessly coupled to the worn local detection and amplification IC.

In an alternate embodiment, the sensor system may be composed of discrete components including the nonlinear meta-stable oscillators set to operate at critical, meta-stability inducing parameters and set to hair-trigger wise switch out of that meta-stable first mode into one or more other modes and to thus distinguish as between even extremely low magnitude incoming signals (e.g., in the 5 pA or less range). One device in accordance with the present disclosure of invention can sense AC electric potentials as low as 1 nV (nano volt) and/or can sense AC electrical currents as low as 1 pA and at a bandwidth of 1 kHz or higher in open environments (due for example to close proximity of the sensor stages containing IC to the scalp or other part of the test subject). The device allows for flexible experimental designs in vivo or in vitro due to its small size (e.g., less than about 500 mm² in area) and light weight. The device may be used for electrophysiology, electrocardiology, electroencephalography, and/or electromyography signal acquisition.

Although some of the examples provided herein are directed to medical diagnosis applications it is within the contemplation of this disclosure to alternatively or additionally apply the here provided teachings to brain-to-machine interfacing applications such as for noninvasive neuronal control of prosthetic devices, of human-controlled other power devices and of brain-to-computer control applications.

An example of a multi-stage sensor system that is suitable for implementing the above goals is provided below, in FIGS. 12 and 13. A signal of interest at a certain frequency range may be selectively detected by using low pass filters within the closed loop of the multi-stage system such that external noise is inherently suppressed. This stands in stark contrast to conventional linear amplification systems, in which the signal and noise at low levels are both amplified together for purpose of detection before various filtering processes are employed to try to reduce the noise portion of the acquired signals.

BRIEF DESCRIPTION OF THE DRAWINGS

FIG. 1A is a schematic perspective view of a subject wearing the small sized, non-linear detection and amplification device in accordance with one embodiment of the present disclosure;

FIG. 2 is an example of EEG waveforms before and at the start of a seizure;

FIG. 5 is a schematic diagram of a signal filtering sub-system;

DETAILED DESCRIPTION

Figure 1B:
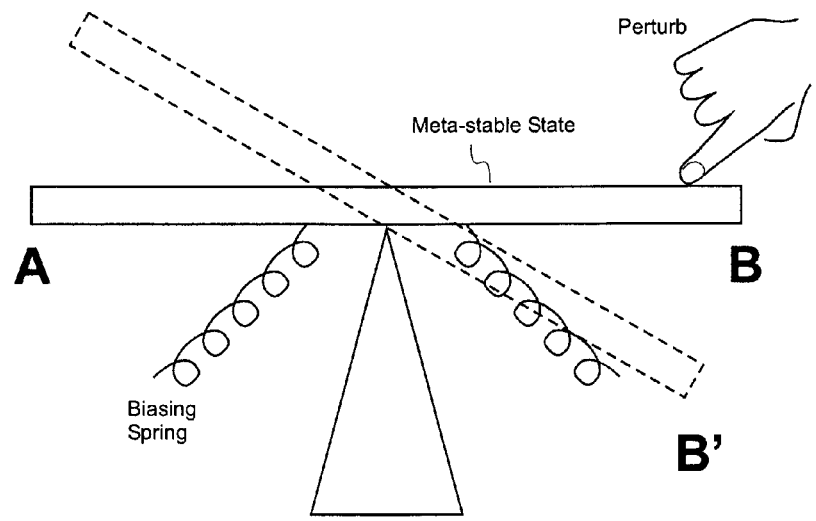
FIG. 1B is a schematic and conceptual illustration of a meta-stable and hair-trigger wise perturbable system.

FIG. 1A is a schematic illustration of a biopotential measurement device 10 that is in accordance with the present disclosure and that has two patient-worn parts, namely, a plurality of electrodes 12 and a light-weight and small-sized data collection unit 30 operatively coupled to the electrodes. As shown, the patient-worn biopotental measurement device 10 is a compact device that may be adhesively or otherwise attached to and/or carried by (e.g., worn) by a person or an animal where both the electrodes 12 and the data collection unit 30 are sufficiently small and flexible to be worn full time while the subject under study (ASUS) goes about his/her/its normal daily activities. The subject-worn, data collection unit 30 is wirelessly coupled to a further data acquisition and processing device 50 for example by way of BlueTooth™ or WiFi wireless coupling. In the particular embodiment that is shown in FIG. 1A, the biopotential measurement device 10 is used as an electroencephalogram (EEG). The electrodes 12 are arranged on the patient's skull and are coupled to be in communication with the nearby and front-end bio-signal detection and amplification unit 30, where like the electrodes, the latter may be worn on and/or adhesively or otherwise attached to the patient's body and connected to the electrodes 12, for example via very thin and thus cosmetically invisible wires. The front-end bio-signal detection and amplification unit 30 detects (senses changes in, and amplifies the sensed changes and optionally digitizes/filters the results) the front-end bio-signals from the electrodes 12, processes the data, and transmits it to the further data acquisition and processing device 50 which in one embodiment, can be a computer/display/tablet 50 either wired or wirelessly coupled to the subject-worn data collection unit 30. The computer/display/tablet/computer 50 may be any appropriate device with a processor (e.g., CPU), a memory, and a user interface that can receive the signals from the data collection unit 30 and thereafter communicate corresponding information to a patient, technician, and/or physician (even if the health care provider is far away).

In the illustrated example of FIG. 1A, flexible wires 13A, 13B respectively connect electrodes 12A and 12B to corresponding, non-reference differential inputs of the front-end bio-signal detection and amplification unit 30 while wire 13C connects a base-located electrode 12C to a reference input (e.g., reference ground point) of the front-end bio-signal detection and amplification unit 30. In the case where the base-located electrode 12C is adhesively or otherwise attached to the skin of the subject (ASUS), the front-end bio-signal detection and amplification unit 30 may also be so attached by a same or similar attachment mechanism and/or the electrode 12C and packaging of unit 30 may be integrally formed such that one attachment mechanism (e.g., adhesive outer sealant plus inner column of conductive gel) affixes both of them to the subject under study (ASUS). The electrical power for the front-end bio-signal detection and amplification unit 30 may be obtained from an elsewhere carried portable battery system (e.g., a rechargeable one); for example one carried in the patient's pocket or strapped on in a lower and more convenient weight bearing part of the body. Coupling 35 represents a wireless coupling of signals, including telemetry signals, between the low weight and small-sized, front-end bio-signal detection and amplification unit 30 (with electrode 12C optionally integrally formed therewith) and a follow up, typically bigger, heavier downstream signals processing unit 50 (e.g., one containing one or more CPU's or other digital signal processing units). The downstream signals processing unit 50 may be carried in the same place as the battery system that powers unit 30 or may be carried separately and instead powered by its own battery system.

Figure 12:
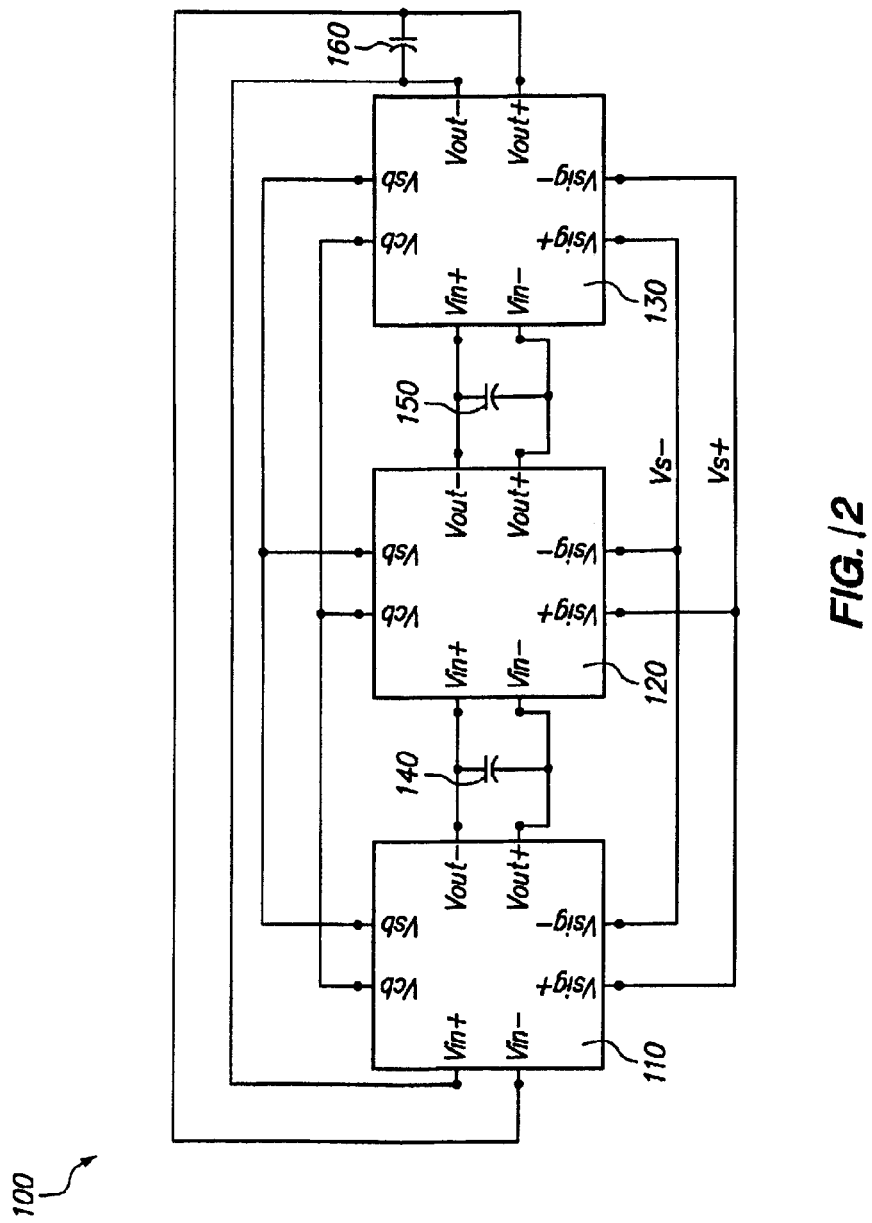
FIG. 12 is a schematic diagram of a 3-stage, meta-stable and hair-trigger wise perturbable system.
Figure 13:
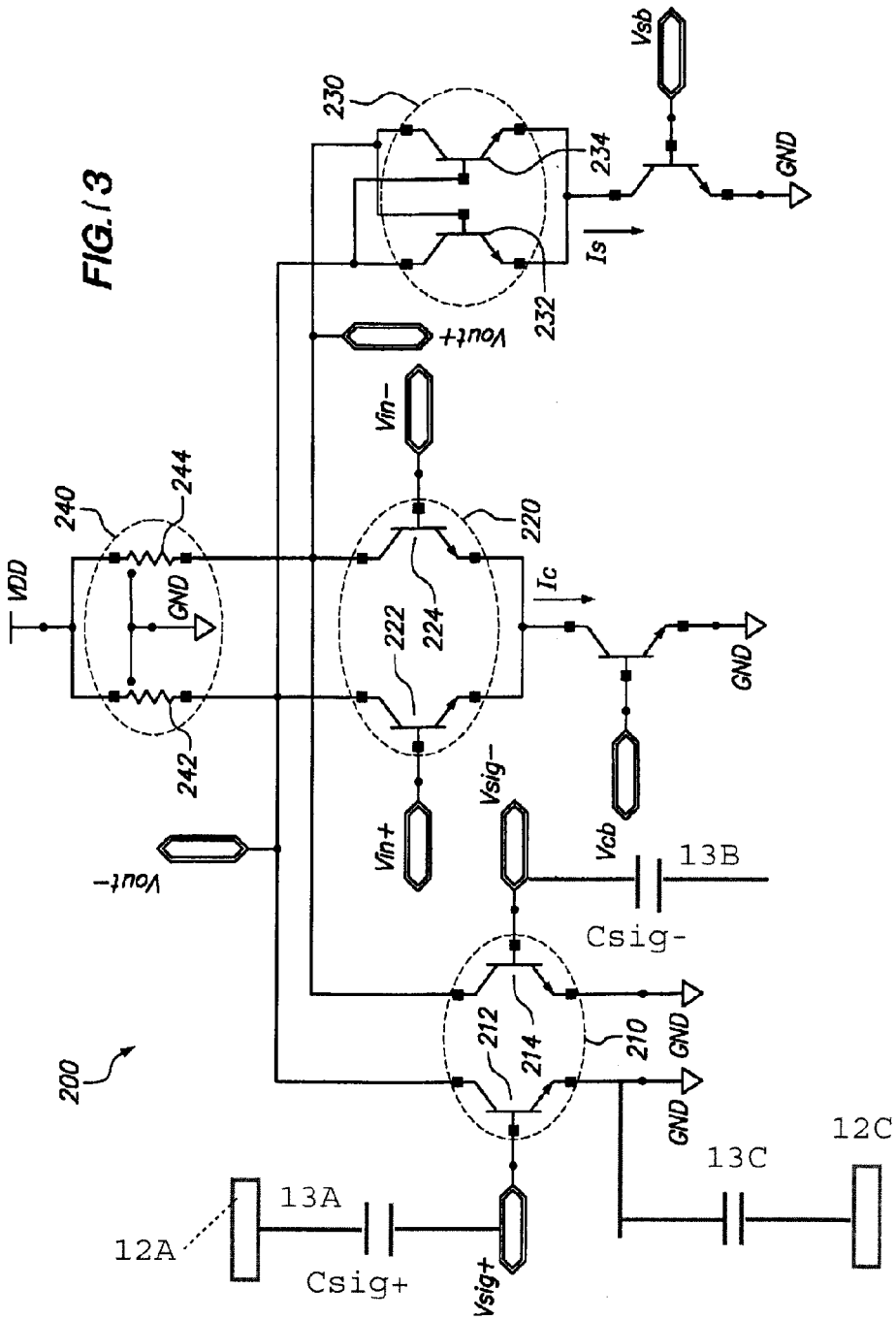
FIG. 13 is a schematic diagram of one of the stages of FIG. 13 and of coupling of corresponding bio-signal acquiring electrodes thereto.

In one aspect, the present disclosure of invention includes utilizing a meta-stable and hair-trigger wise perturbable system such as the multi-sensor stages system described in FIGS. 12 and 13 to sense biopotentials (or currents) in human/animal bodies where such signals were previously not individually detectable (e.g., without extensive signal averaging). These adaptations include design of the electrodes 12 with considerations such as size, surface area, and stable mounting given the high fidelity nature of the signals and their connections being optimized to match the needs of the multi-sensor stages system and adjusting the sensor components to produce the output relevant for input signal, converting the analog signal from the sensor to a digital output for further signal processing steps.

The example of FIG. 12 is merely that; an example. In a broader sense, the present disclosure of invention recognizes that nerve firings are all-or-nothing types of events and detection of the latter does not require an all-linear signal sensing approaches. Instead a meta-stable and hair-trigger wise perturbable system may be used where the switch between clearly distinguishable operating modes of the meta-stable and hair-trigger wise perturbable system is taken to indicate a corresponding change in sensed input signals.

By way of a first example of what might be considered to be a meta-stable and hair-trigger wise perturbable system, consider the common coin (where the coin—or similarly shaped cylinder of relatively small height and relatively large top and bottom circular surfaces—is to land on a smooth flat surface—for example the floor). One of the players is asked to call heads or tails. It is unobvious to call "edge" as a possible landing state for the tossed coin even though there is that remote possibility (that the coin lands on and remains standing on its edge rather than flat faced on its heads or tails side). The reason the call is unobvious and almost never made is because the on-edge-standing state of the coin is a highly meta-stable and hair-trigger wise perturbable state when the coin is landing on a smooth flat surface. Any small vibration, breeze, or other applied force can easily send the on-edge-standing coin cascading into a more stable one of its flat faced and alternative, on heads or on-tails states. And thus the coin appears to invariably end up in only its on heads or on-tails state even though for one brief instant it landed on its meta-stable edge.

The present disclosure of invention seeks to take advantage of the extreme sensitivity of such a meta-stable and hair-trigger wise perturbable system where, for example, a coin is intentionally set and balanced on its edge so that any small external perturbation sends it cascading towards its clearly distinguishable, other and more stable states, namely, its on heads or on-tails states. However, there is a little more to the use of the underlying concept. Consider the hypothetical see-saw example of FIG. 1A. The triangle represents a fulcrum for a balance beam having mass and respective first and second ends, A and B. In its meta-stable and hair-trigger wise perturbable state where the beam is balanced to rest on the fulcrum with ends A and B forming a perfectly horizontal line, symmetry keeps the balance beam in the illustrated (illustrated by a solid elongated rectangle) meta-stable and hair-trigger wise perturbable state. However, any small perturbation; for example the slight and momentary touch of a finger, can tip the beam out of this delicately balanced state and send it cascading towards one of its more stable (lower energy) states; for example where the B end heads towards the illustrated dashed B' position (B primed position). As those who have used playground see-saws will appreciate, once the see-saw is tipped (as an example of a balance beam having mass and inertia) into one of its substantially more stable states of being either heads down or tails down (in other words, one of the first and second ends, A and B touching the ground)—and once the beam has given up some of its energy due to collision with the ground, the see saw tends to stay that way. There is not enough energy to return it back to its horizontally but delicately balanced meta-stable state.

Still referring to FIG. 1B, the hypothetical see-saw of the illustrated example is slightly modified by adding a symmetrical set of special biasing springs to it. The spring factor (k) of the springs is set such that the biasing springs exert essential no counterforce to the balance beam when the latter is in its delicately balanced, horizontal, meta-stable and hair-trigger wise perturbable state (A and B forming a horizontal line). However, after the beam is perturbed by a slight momentary touch (an example of a sensed, weak signal event), the restoring force of the springs increase non-linearly such that the downward heading end (e.g., B') is restrained from going all the way down to and colliding with the ground. Instead an oscillation is induced by the triggering event of the slight momentary finger touch and by the hypothesized behavior of the biasing springs.

As the oscillation continues (assume no friction losses in this hypothesized example) assume that the finger comes to momentarily touch the beam one more time (again with a very delicate, slight and momentary touch) just as the system is passing through the top of its energy hill (see FIG. 1C, explained immediately below). Again the system is in a state where the addition of just a slight amount of additional energy (the momentary finger touch) can send it cascading into a distinguishable different oscillation pattern (for example to a higher frequency; because in one example, its contained energy has been increased by constructive interference due to the second finger touch). It is thus seen from the given examples that the addition of very small amounts of input energy (e.g., the finger touch) can send a meta-stable and hair-trigger wise perturbable system into different modes of oscillation (e.g., different and easily distinguishable frequencies) due to constructively or destructively interfering, couplings of small amounts of input energy.

As an alternative to the above hypothesis where the second very delicate, slight and momentary finger touch constructively interferes with the system and sends the system into a second oscillatory mode of different frequency, it is possible that the second finger touch instead destructively interferes with the system and sends it into a non-oscillatory mode where the beam returns to its on edge, balanced state; ready to be perturbed again. In either case, the meta-stable and hair-trigger wise perturbable system is switched between clearly distinguishable operating modes. Each change from one clearly distinguishable operating mode to another clearly distinguishable operating mode can be pre-correlated to a specific magnitude of input signal (or to a finite range of input signals) and/or to a type of input signal (e.g., constructively interfering versus destructively interfering) by way of calibrating experiments performed before the meta-stable and hair-trigger wise perturbable system is put into filed use. The results of the calibrating experiments can be stored in a computer or lookup table (LUT) and then used in the field to back correlate from an observed (determined) change of operating mode of the perturbable system to the magnitude and/or type of input signal (or range of input signals) that likely caused the observed (determined) change. Thus, even if the input signal is of extremely small strength and yet sufficient to perturb the perturbable system in an observable manner, the input signal can be detected.

Figure 1C:
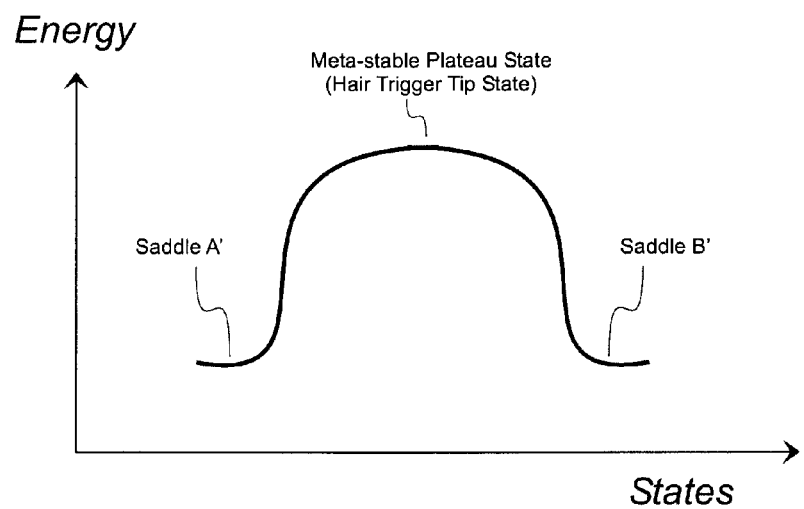
FIG. 1C is a graph for use with FIG. 1B for explaining the possible stable and meta-stable states of a meta-stable and hair-trigger wise perturbable system.

Referring next to FIG. 1C, this is an exemplary graph of a multi-state system that has at least two, low energy stable states (referred to also as saddle points) and a higher energy plateau between them (referred to also as the meta-stable and hair-trigger wise excited-state). It will be appreciated by those skilled in the art of nonlinear chaotic systems that the illustrated system can remain in steady state at any energy level that has a zero slope (more specifically, at either of the bottoms of the saddle points or at the flat top of the exemplary energy hill). However, at points where the system energy curve has a non-zero slope, the system tends to naturally shift to a lower energy state (e.g., towards one of its saddle points). The amount of energy needed to perturb the system away from its top-of-the-hill and meta-stable state and into a down-sliding mode is relatively small. Thus the latter is referred to as a meta-stable and hair-trigger wise perturbable state. The amount of energy needed to perturb the system out of one of its saddle points and get it back up to the top-of-the-hill state is substantially larger. Thus the saddle points are respective first and second substantially more stable states. A system with just two saddle points and just one meta-stable plateau between them is just an example. It is within the contemplation of the present disclosure to have alternative systems with more than two saddle points and more than just one meta-stable plateau therebetween, where after the system settles into one of its saddle points, it is automatically reset to or oscillates back to passing over one of its meta-stable plateaus, whereat it is sensitive to being greater perturbed in behavior by even small amounts of input energy (e.g., a slight finger touch).

More specifically, the present disclosure of invention provides a system which repeatedly places itself (or at least one of its stages) into the meta-stable and hair-trigger wise perturbable state so that it can detect (sense) the input of a very weak input perturbation (a very weak input signal). In one embodiment, the oscillatory frequency of the system shifts each time it is subjected to a slight perturbation and while one of its stages is in a respective meta-stable and hair-trigger wise perturbable state. (See briefly FIG. 12 which illustrates a multi-stage such system.)

With the above as additional background, the present description proceeds to an overview of one exemplary, but not limiting embodiment.

FIG. 2 is an example of an EEG data that could be displayed on the computer/display/tablet computer 50 before and when a patient is experiencing a seizure. The data shows a period A where the signal amplitude is low but not null, followed by a period B where the signal amplitude shows a noticeable increase in magnitude. In period B, the patient is having a seizure. Period A shows what happens to the biopotential measurements just before the seizure actually happens, and may provide a non-null warning that a seizure is about to happen. Unfortunately, currently available EEG devices do not have a high enough signal-to-noise ratio to effectively read the low-amplitude & high frequency signals of period A, and the data in this period cannot therefore be utilized by conventional means. Hence, the non-null seizure warning signs go undetected and no action (e.g., any preventative or preparatory measure) can be taken until the patient is in period B, by which point he or she is already experiencing a seizure. Therefore the data in period B or earlier will be used only for monitoring purposes rather than for predicting purposes when conventional devices are used.

Figure 3:
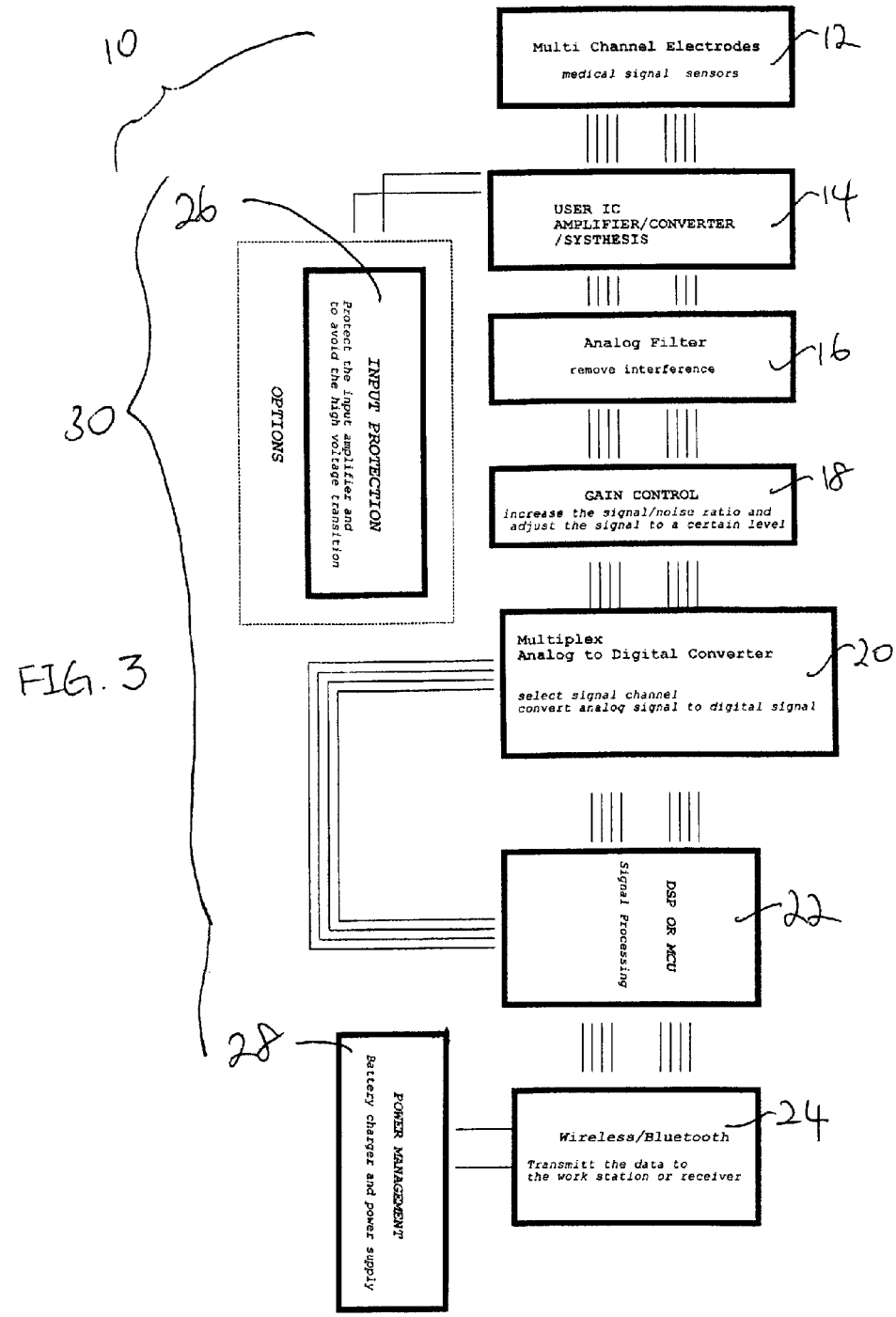
FIG. 3 is a schematic diagram of a multi-electrode bio-signals detecting system in accordance with the present disclosure.

FIG. 3 is a functional block diagram of a biopotential measurement device 10 in accordance with the present disclosure of invention. As shown, the biopotential measurement system 10 includes multi-channel electrodes 12 and the data collection unit 30. The data collection unit 30 may include sensor stages, such as ones similar to what is disclosed in U.S. Pat. Nos. 7,420,366, 7,528,606, 8,049,570, and 8,212,569. The meta-stable oscillatory modes of these multi-sensor stage systems are rapidly and distinguishably changed due to even minute inputs (e.g., 1 pA disturbances). The electrodes 12 pass the signals (e.g., AC coupled signals) to the easily-perturbed sensor unit 14. Within the easily-perturbed sensor unit 14 there may be frequency and/or phase converter (not shown) that detects and distinguishes between the different oscillatory modes of meta-stable and hair-trigger wise perturbable systems within the sensor unit 14 and converts the sensed frequencies and/or phases into corresponding output voltages. The frequency and/or phase converter (not shown) may be followed by a gain control unit 18, which increases the signal to noise ratio and adjust the signals so they normalize to a certain predetermined level. The gain control unit 18 may drive an A/D converter 20, which may be a multiplex A/D converter that selects a specific one or few signal channels and converts the corresponding analog signals to digital ones for further processing by the downstream Digital Signal Processor/Microcontroller Unit 22. The converted and once digitally-processed digital signals can thereafter be transmitted (e.g., wirelessly) by a transmitter 24 to a receiver provided within a larger (e.g., heavier, one with more battery and data processing power) package that also contains computer/display/tablet computer 50. The transmission may be done wirelessly (either analog or digital and optical or electrical). Although the diagram shows generally the components that make up the bio signals measurement device 10, it will be understood that various modifications are possible in view of the teachings of the present disclosure. For example, an input protection means 26 may be added to protect the input sensor unit 14 and amplifier/converter/filter unit 16 and to avoid high-voltage (e.g., static electricity) transitions. In addition, the order in which the following processes such as analog filter 16, gain control 18, digital converter 20, digital signaling processing units 24 can be altered in order to improve the signal fidelity or to lower the power consumption.

Figures 4A, 4B, 4C:
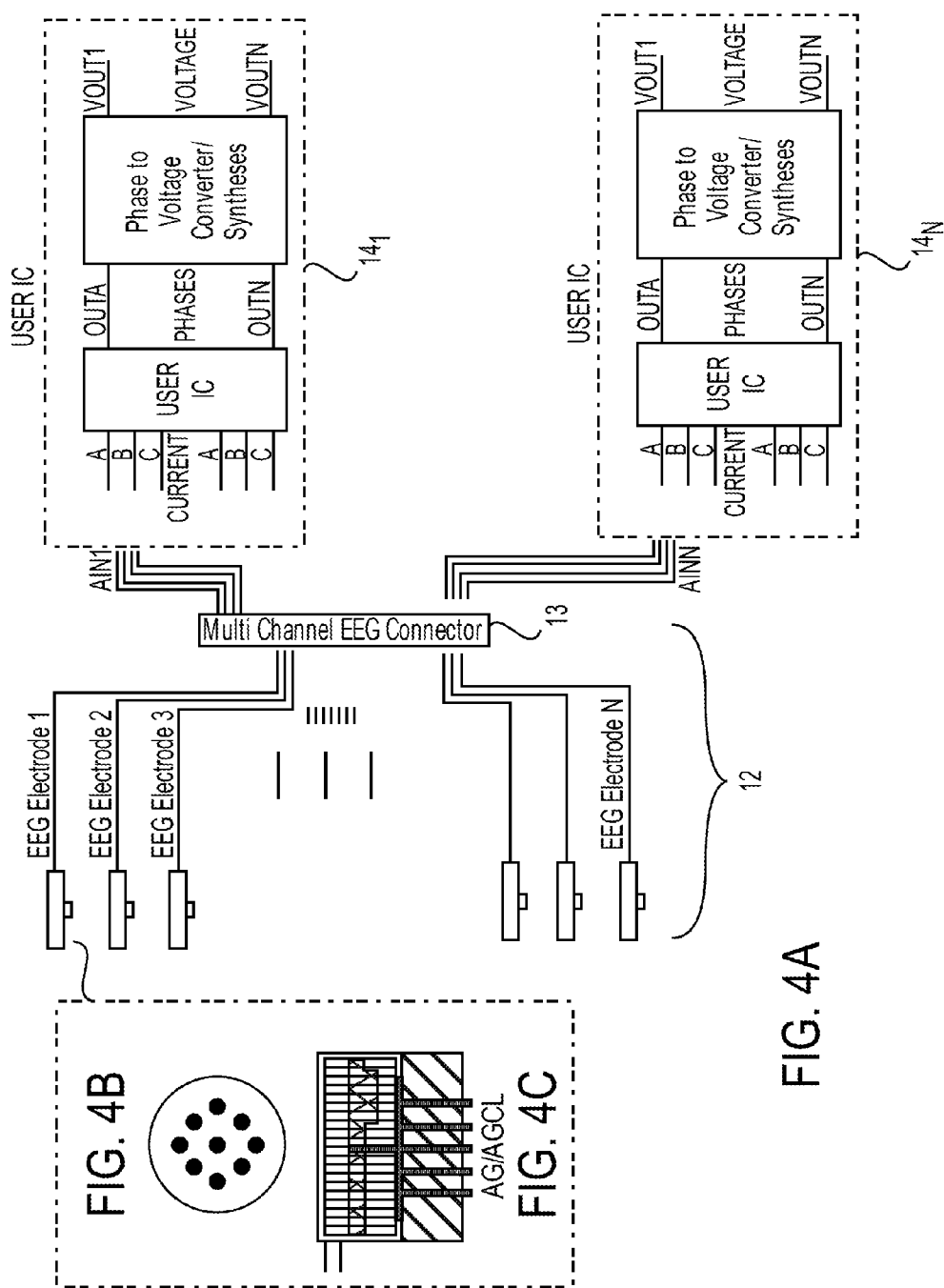
FIG. 4A is a schematic diagram showing further details of one embodiment of the system depicted in FIG. 3.
FIG. 4B shows a bottom plan view of a multi-needle electrode structure in accordance with one exemplary embodiment.
FIG. 4C is a side sectional view of a multi-needle electrode structure such as that of FIG. 4B.

FIG. 4A is a schematic diagram of an exemplary embodiment for the multichannel electrodes 12 of FIG. 2. As shown, there are N number of electrodes 12 in a single bio signals measurement device 10 (where N can be 2 or substantially larger than 2). The plurality of electrodes 12, which may be attached to different parts of the subject, feed signals to a multi-channel EEG connector 13. The multi-channel EEG connector 13 is capable of generating N signals $AIN_1$ through $AIN_N$ and dividing the signals between multiple sensor/converter ICs $14_1 \ldots 14_N$. Each sensor/converter IC 14 generates N output voltages, shown as $V_{out1} \ldots V_{outN}$. Each of the sensor/converter ICs $14_1 \ldots 14_N$ includes one or more of the multi-sensor stage systems described herein.

FIG. 4B is a top plan view of an exemplary electrode 12". FIG. 4C is a side view of the electrode 12". The electrodes 12" may have skin surface contact areas that are much smaller than that of conventional electrodes and they are shielded by dielectric materials (or stretchable materials for flexible shaping on the skin) and they connect to silver or silver/chloride coupling wires, which are also coupled to the sensor core.

FIG. 5 is a schematic diagram of an embodiment of the analog filter 16 that receives the output voltages from the sensor/converter IC 14 ($V_{out1} \ldots V_{outN}$) and removes undesirable interference. As shown, the analog filter 16 includes a plurality of operational amplifiers $50_1$ through $SO_N$ to receive output voltages $V_{out1} \ldots V_{outN}$ and generate filter output voltages $FV_{out1} \ldots FV_{outN}$, respectively. Use of operational amplifiers with reactive components (e.g., capacitances, inductances) as signal filters are well known and thus are not detailed here. The converter preferably converts the nonlinear responses of the multi-stage-sensor of the input signals to output voltage levels that reflect the respective strengths of the weak input signals that perturb the meta-stable and hair-trigger wise perturbable sensors into respective oscillatory modes.

Figure 6:
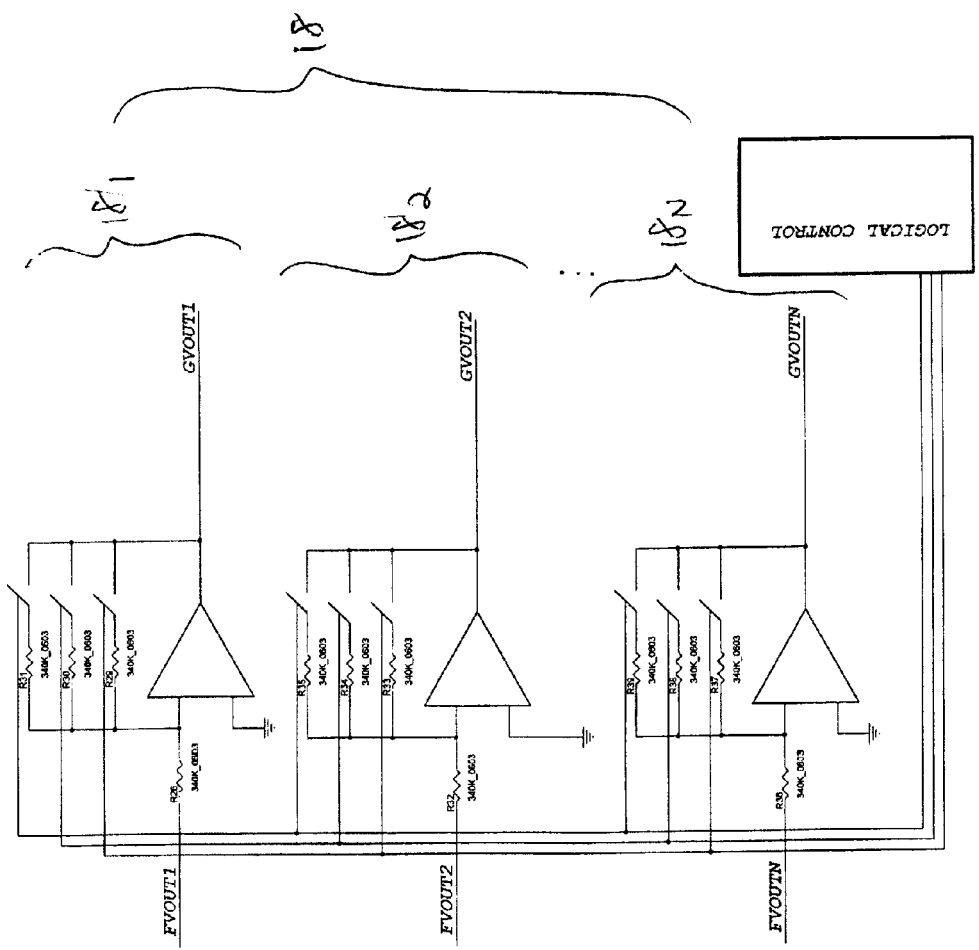
FIG. 6 is a schematic diagram of a programmable post-detection, amplification sub-system.

FIG. 6 is a schematic diagram of an embodiment of a programmable gain control unit 18 to increase the signal-to-noise ratio or adjust the signal level. The gain control unit 18 includes a plurality of subsections $18_1$ through $18_N$ that receive the filter output voltages $FV_{out1} \ldots FV_{outN}$ and generate gain output voltages $GV_{out1} \ldots GV_{outN}$. As will become clearer below, the nonlinear multi-stage sensor systems exhibit an intrinsic oscillation when no signal (e.g., 0 pA) is present. As long as the input signal is outside a predetermined dynamic range where the multi-stage sensors are sensitive, the effect of input signal perturbation is not noticeable. On the other hand, when the input signal is within the predetermined dynamic range where the multi-stage sensor is sensitive, the effect of input signal perturbation is most noticeable. Therefore, in accordance with one aspect of the disclosure, an iterative logic process is used to determine, based on the observed change of state of the meta-stable multi-stage sensor system, the amplitude of the input signal otherwise, the signal will be tested again for another sensor set for a lower dynamic range. This type of gain control can be automated.

Figure 7:
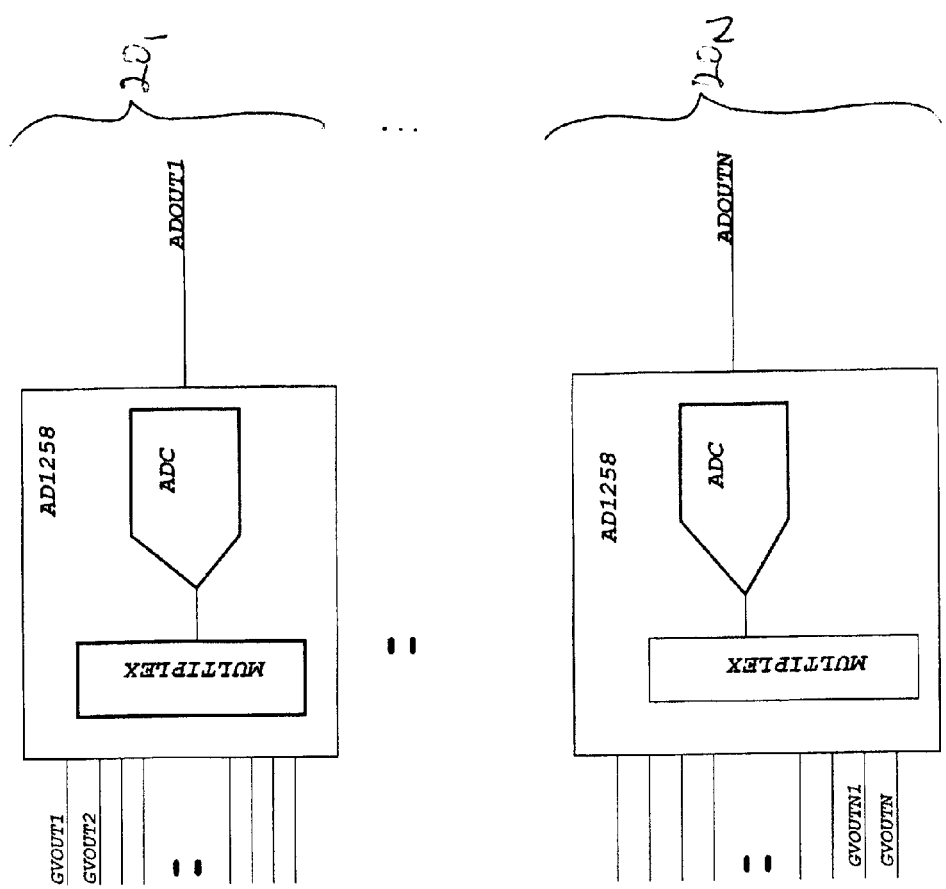
FIG. 7 illustrates post-detection conversion into the digital signals domain.

FIG. 7 is a schematic diagram of an embodiment of the multiplex A/D converter 20 to select signal channels and to convert the analog signal to digital. The multiplex A/D converter 20 may have N subsections $20_1$ through $20_N$. The plurality of gain output voltages $GV_{out1} \ldots GV_{outN}$ generated by the gain control unit 18 is fed into each of the subsections $20_1$ through $20_N$ and may be converted into digital signals $AD_{out1} \ldots AD_{outN}$.

Figure 8:
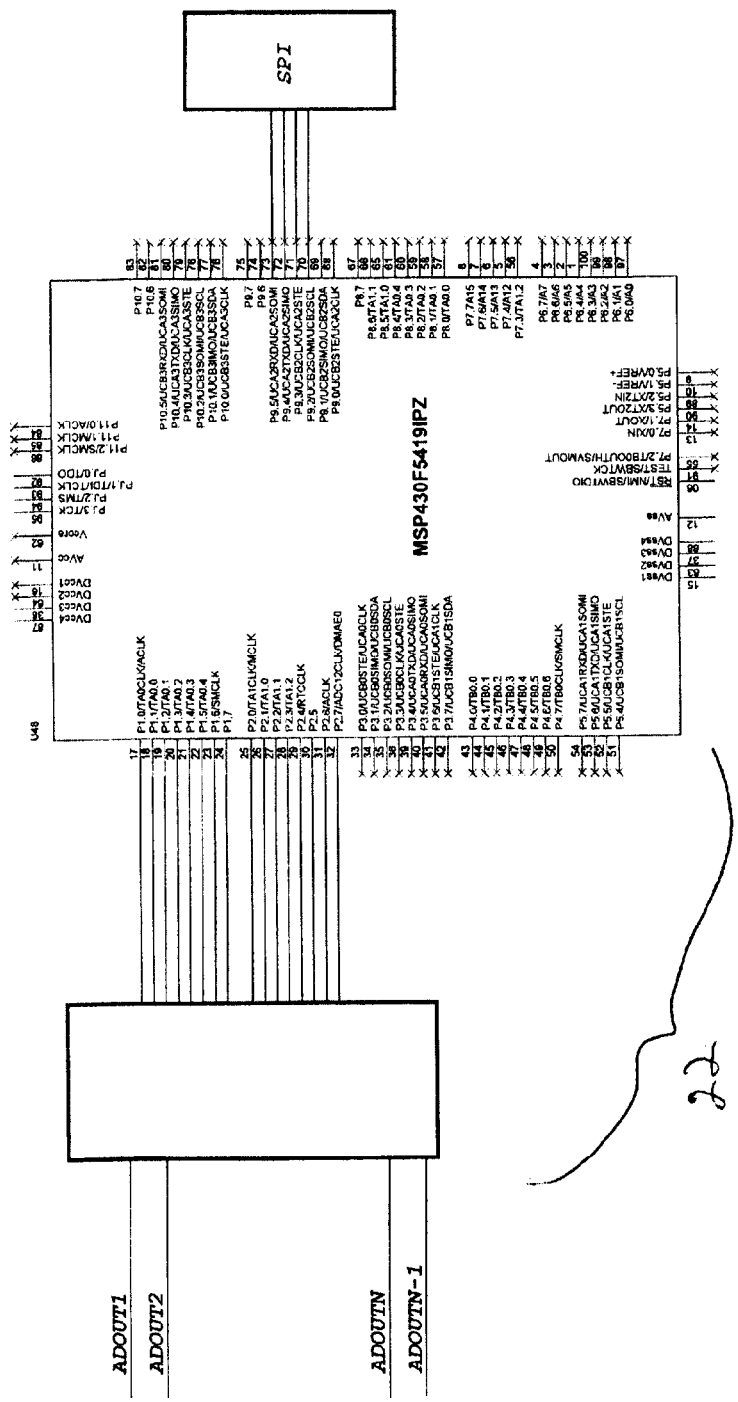
FIG. 8 illustrates a post-detection digital signals processing unit.

FIG. 8 is a schematic diagram of an embodiment of Digital Signal Processor 22. The figure shows an example of a commercially available digital signal processor (e.g., one made by Texas Instruments) that may be used to receive and process the digital signals $AD_{out1} \ldots AD_{outN}$.

Figure 9:
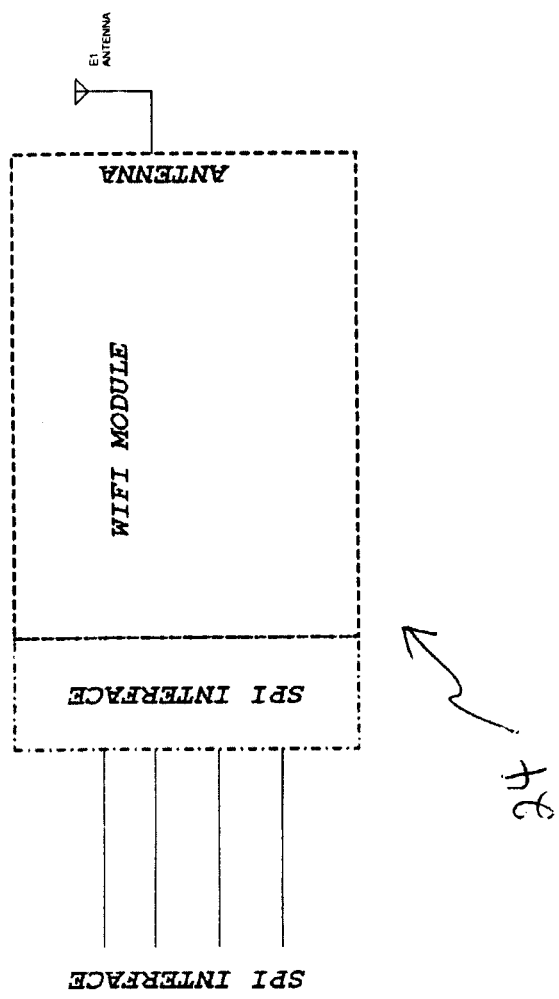
FIG. 9 is a schematic diagram of a wireless signals intercoupling sub-system.

FIG. 9 is a schematic diagram of an embodiment of the transmitter 24. The Digital Signal Processor 22 forwards signals to a Serial Peripheral Interface (SPI) bus, which interfaces with a WiFi module in the transmitter 24. The measurement data is then transmitted to an external device, such as the computer 50

Figure 10:
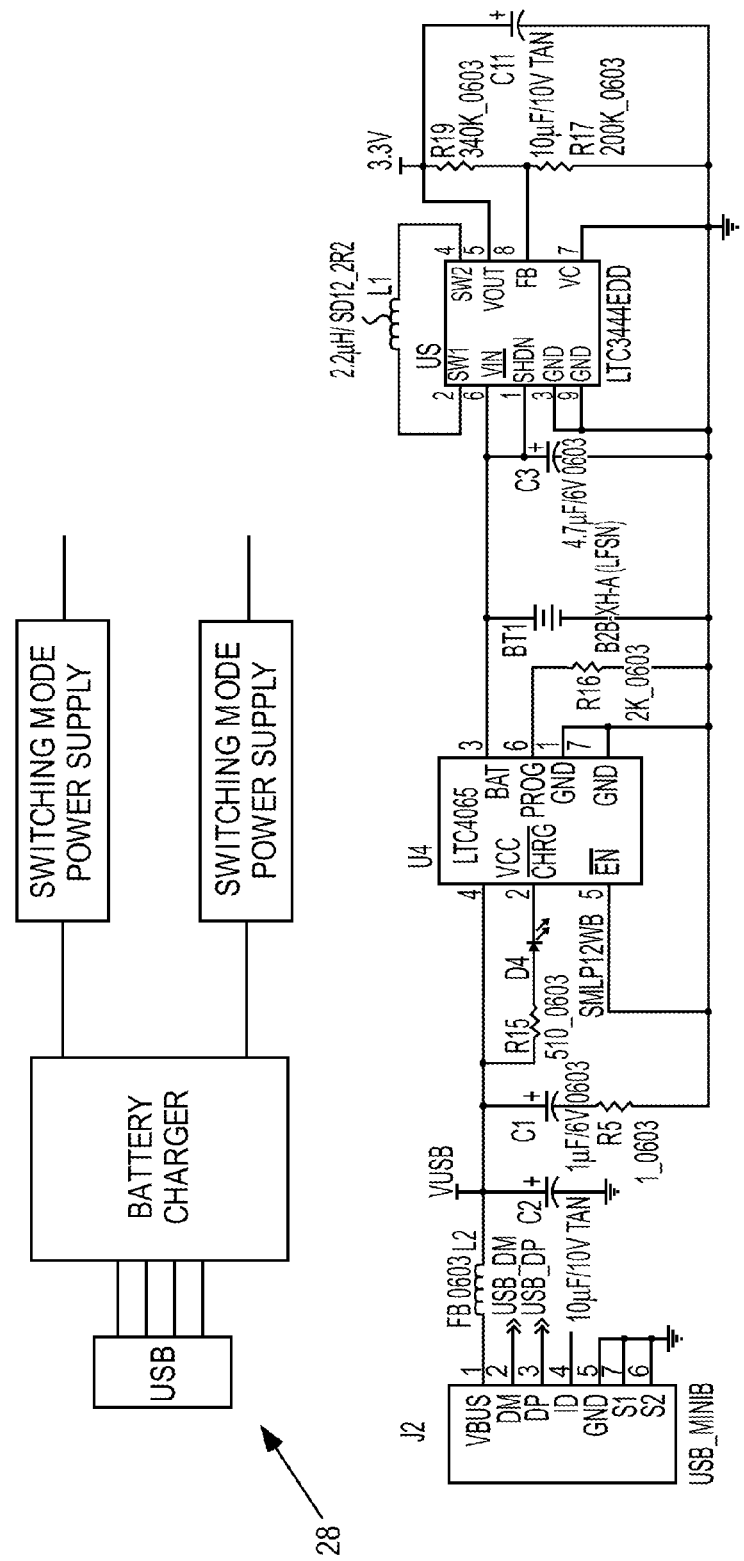
FIG. 10 is a schematic diagram of a portable power sub-system.

FIG. 10 is a schematic diagram of an embodiment of the power management unit 28. The power management unit 28 may work with a portable or non-portable power source. In some embodiments, a switching mode power supply may be used, such as the one shown at the bottom of FIG. 10.

Figure 11:
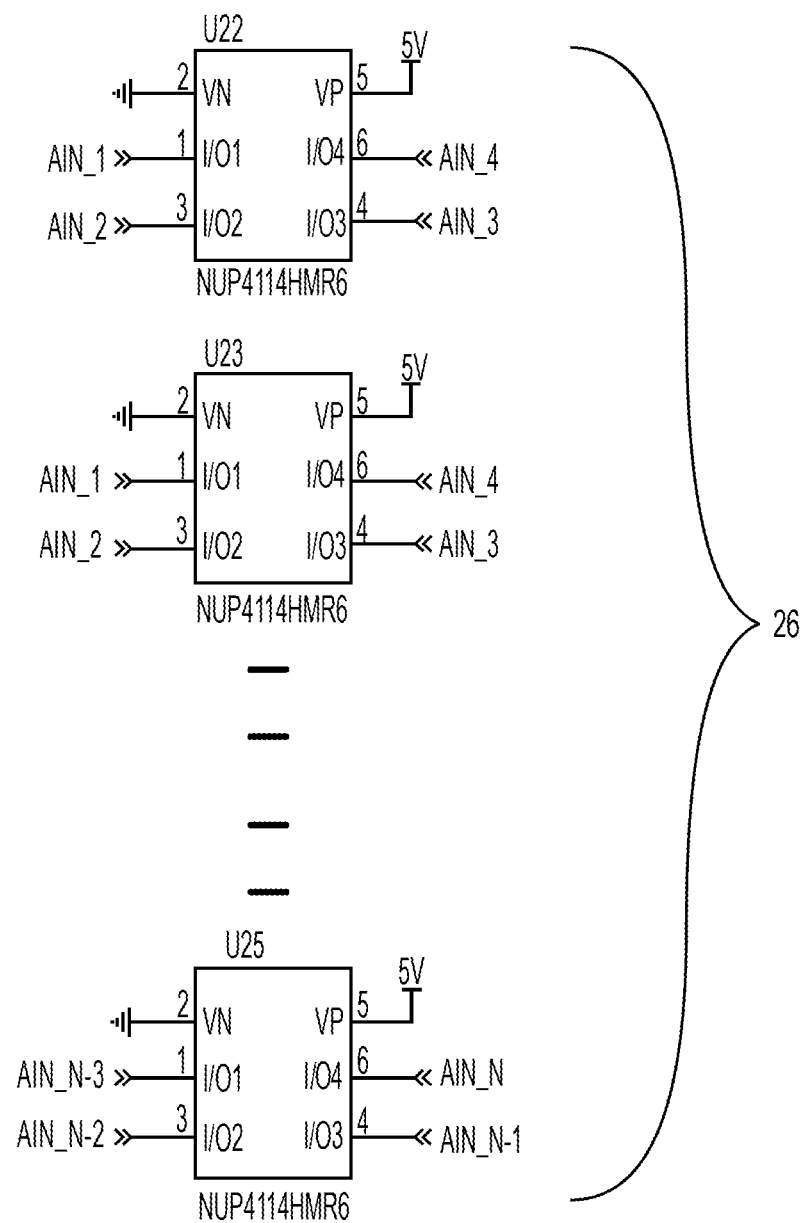
FIG. 11 is a schematic diagram of an input protection circuit.

FIG. 11 is a schematic diagram of an embodiment of a system for input protection unit 26. The input protection unit 26 protects against electrostatic discharges or high voltages. As shown in FIG. 4A, there are N amplifier/converter ICs (labeled $14_1$ through $14_N$) that receive the signals $AIN_1$ through $AIN_N$ from the multi-channel EEG connector 13. These signals are fed into various parts of the input protection unit 26, as shown.

FIG. 12 is a schematic diagram of an example of a multi-stage microcircuit sensor system 100 that may be used to implement the biopotential measurement device 10. The multi-stage sensor system is comprised of a closed loop of nonlinear current splitters (which may be seen as electronic see-saws in a certain respect) where the loop of cascaded sensor stages go into a first metastable oscillatory mode due to background noise when properly balanced and not perturbed by any further input signal. As an example, the illustrated multi-stage sensor system 100 comprises 3 or more sensor stages, more specifically, the illustrated three stages, 110, 120, and 130. Referring to FIG. 13, each of the stages may include a first and input receiving operational transconductance amplifier (OTA) 210, a current-splitting (coupling) OTA 220, and a non-linear operation mode biasing OTA (a weak latch or flip flop) 230. The sensor is configured to detect minute electrical current changes at the input port provided by the first OTA. More specifically, the second OTA 220 (the current-splitting section) may be thought of as being akin to the balance beam of the FIG. 1B. It can be tipped so that one or the other of identical transistors 222 and 224 carries most of the current that is sunk as tail current Ic. Although not shown in FIG. 13, the mis-balancing of the main current-splitting section (second OTA 220) may be given the electronic version of mass and inertia by use of reactive components such as the capacitances 140, 150, 160 shown in FIG. 12. The first and input receiving amplifier (first OTA 210) may be thought of as being akin to the finger of concept FIG. 1B in that it perturbs the current splitting function otherwise carried out by the second OTA 220. The third and mode biasing OTA 230 may be thought of as being akin to one of the biasing springs of concept FIG. 1B. In this embodiment and counter-biasing weak latch (a second OTA 230) is provided in one of the next-sequence sensor stages (see FIG. 12).

Each stage 110, 120, and 130 may be described as an essentially symmetrical current splitter (except that the cross coupling of base to collector in OTA 230 prevents that OTA from operating in perfectly split (balanced) current mode). By coupling one stage to the next, the imbalanced state of one electronic see-saw (OTA 220) ripples from a first stage (e.g., 110 of FIG. 12) to become amplified in a next stage (e.g., 120 of FIG. 12) and so on (e.g., as carried out by 130 of FIG. 12) repeatedly around the loop so that a first oscillatory mode is established even when there is no measurable input signal (e.g., 0 pA). Thereafter even a slight perturbation (e.g., a 1 pA difference in current inputs at Vsig+ and Vsig−) as applied at the right moment of sensitivity of any one stage (e.g., when that stage is at or substantially near to the peak of its energy hill of FIG. 1c) can become rapidly amplified so as to switch the loop into a different and distinguishable, second oscillatory mode (e.g., one having a distinguishable second frequency of oscillation and/or one having a distinguishable second waveform). The overall system 100 may be modeled as an appropriately damped bi-stable system operating in accordance with a hyperbolic tangent function, where the latter results from the use of the nonlinear operational transconductance amplifiers (OTAs). The entire dynamics may be derived from Kirchhoff's current junction laws as applied for the output nodes, $V_{o1+}$ and $V_{o1-}$, shown in FIG. 13, and it is given as:

$$C_L * dV_{o1}/dt = -gV_{o1} + I_s \tan h(\beta_s V_{i1}) \quad (1)$$

where g, $I_s$ and $\beta_s$ control the bi-stability of the energy function of the subunit. g, or $1/R_L$, is a linear conductance, $C_L$ is the total parasitic capacitance at the output node, $V_{i1}$ is the differential voltage input of the subunit (i.e. $V_{i1} = V_{i1+} - V_{i1-}$), and $V_{o1}$ is the differential voltage output of the subunit (i.e. $V_{o1} = V_{o1+} - V_{o1-}$). When the three stages are unidirectionally coupled per the implications of FIGS. 13 and 12, the following equations describe the dynamical behavior of the sensor system:

$$C_L * \tilde{V}_1 = -gV_1 - I_c \tan h(\beta_c * V_3) + I_s \tan h(\beta_s * V_1) + \in_{in}$$

$$C_L * \tilde{V}_2 = -gV_2 - I_c \tan h(\beta_c * V_1) + I_s \tan h(\beta_s * V_2) + \in_{in}$$

$$C_L * \tilde{V}_3 = -gV_3 - I_c \tan h(\beta_c * V_2) + I_s \tan h(\beta_s * V_3) + \in_{in} \quad (2)$$

where $V_i$ represents voltage output of the i-th stage in a unidirectionally coupled 3-stage multi-stage sensor system, $I_c$ and $I_s$ are bias currents which control the non-linear terms in the system, $\beta_c$ and $\beta_s$ are device parameters, and $\in_{in}$ is the external current (or voltage supplied as hyperbolic tangent forms) input signal.

The input for the last, preferably odd-numbered stage (equation) is opposite in polarity to the other two stages in the ring to take advantage of the enhanced asymmetry in the oscillation characteristic, mainly the duty cycle difference of the oscillations. This, in turn, enhances the sensitivity of the sensing system. Further, each of the sensor stages may include fully differential inputs and outputs, as shown in FIG. 13.

FIG. 12 also shows filter capacitors that may be optionally connected as inertia providing reactive components between each of the sensor stages. Capacitor 140 is connected between first stage 110 and second stage 120, capacitor 150 is connected between second stage 120 and third stage 130, and capacitor 160 is connected between third stage 160 and first stage 110. Capacitors 140, 150, and 160 may be off-chip capacitors, in embodiments where sensor stages 110, 120 and 140 are all contained in a monolithically integrated microchip. Capacitors 140, 150, and 160, each of the value $C_L/2$, where $C_L$ is the capacitance value in equation 2, are connected across each of differential outputs. The input nodes (shown in FIG. 13), $V_{sig}+$ and $V_{sig}-$, from each stage are tied together in the way shown in FIG. 12. For one of the stages, the connection of the two nodes is reversed to fit the sign reversal of the last equation in equation 2, to make the circuit more sensitive. Although the filter capacitors 140, 150, 160 are shown as fixed value devices in the example of FIG. 12, it is within the contemplation of the disclosure to replace one or more of them with variable capacitance devices and/or to include variable inductance elements each tunable by an external data processing sub-system whereby the meta-stable state of the system 100 may be fine tuned for specific applications.

FIG. 13 shows a schematic diagram of an embodiment of a sensor stage 200 in accordance with the Coupled Bi-Stable Microcircuit System for Ultra-Sensitive Electrical and Magnetic Field Sensing (U.S. Pat. No. 8,049,570). Sensor stage 200 includes an OTA 210 including identical NPN bipolar junction transistors (BJTs) 212 and 214, a coupling OTA 220 with identical BJTs 222 and 224, a non-linear OTA 230 with identical BJTs 232 and 234, and a resistive load 240 including identical resistors 242 and 244. Transistors 212 and 214 may be used as part of a circuit for receiving an external input signal (e.g., a see-saw tipping signal) as a differential AC current signal by way of respective input capacitances Csig+ and Csig−. When this differential AC current signal is at 0 pA, identical BJTs 212 and 214 draw identical currents through their collectors and thus do not tip the balancing of current splitting operations in the main OTA 220. Assuming for a moment that Vin+ equals Vin−, then identical BJTs 222 and 224 also draw identical currents at that instant. In one embodiment, identical BJTs 222 and 224 are not the same size as identical BJTs 212 and 214 and more specifically, BJTs 222 and 224 are bigger in size such that OTA 220 sinks more current in response to a fixed input signal than does OTA 210 for that same fixed input signal. Also, although not shown, separate DC biasing means may be provided for OTA 210 such that its transistors 212/214 operate at a different biasing point than do the transistors 222/224 of OTA 220. In one embodiment, and for all of OTA's 210, 220 and 230, their respective differential pair transistors: 212/214, 222/224 and 232/234 are biased to normally operate in a near-threshold nonlinear range of their respective IN curves rather than in the linear or saturated portions such that their respective responses to corresponding differential input signals are nonlinear and non-saturated. The DC biasing means may include one or more temperature-compensated current sources (each having a relatively high output impedance) and driving the respective bases of respectively biased polar transistors. Those skilled in the art know how to construct precision and temperature-compensated current sources.

Unlike OTA's 210 and 220, the third OTA 230 has its identical BJTs 232, 234 cross-coupled in a collector of one being connected to the base of the other configuration so as to bistably bias the balance slightly one way or the other; this corresponding to one of the biasing springs of the conceptual diagram of FIG. 1B. In one embodiment, the transistors 232/234 of OTA 230 are different in size than that of either of the respective transistor pairs of OTA's 210 and 220 and more specifically, they are smaller in size so as to draw even less of the current drawn from the shared load resistors 242/244.

The closed loop connecting of the 3 stages in FIG. 12 induces a first oscillatory mode when the input differential current signal is at 0 pA for each of the Vsig+ and Vsig− input terminals of the three stages. However, if the input AC differential current signal increases, say for example to 1 pA, this can drastically tip the balance in at least one of the, at times, meta-stable and hair-trigger wise perturbable stages 110, 120, 130 and thus drive the closed loop system 100 into a substantially different and thus easily distinguished, second oscillatory mode, for example one having one or more different frequencies and/or one having different waveforms. Each of the different and thus easily distinguished oscillatory mode (generally there are more than two such modes) is cross-correlated with a respective input strength range. For example a first strength range may be >0 pA to ≤1 pA; a second strength range may be >1 pA to ≤3 pA; a third strength range may be >3 pA to ≤5 pA; a fourth strength range may be >5 pA to ≤10 pA; and so on.

In one embodiment, the respective tail currents $I_c$ and $I_s$ of OTA 220 and OTA 230, respectively, can be used for biasing their respective differential pair transistors 222/224 and 232/234. For each stage, there may be a same or different biasing configuration for each of the respective two tail currents. The setting of the biasing tail currents may include use of a resistor and of a respective NPN transistor. The base of biasing NPN transistor of each is connected to either node $V_{cb}$ or $V_{sb}$ (shown in FIG. 13) of each stage. The $V_{cb}$ and/or $V_{sb}$ biasing resistor(s) may include those off-chip and they can be replaced by variable resistor(s), to thereby variably set the value of each tail current for example in the following way:

$$I \sim (V_{dd} - 2 \ast V_{be}) R_c$$

where $V_{dd}$ is the supply voltage, $V_{be}$ is the forward-biased voltage of the base-emitter junction of NPN transistors (assuming they have the same $V_{be}$), and $R_c$ is the value of resistor.

Referring back to FIG. 13, each of two hyperbolic tangent terms in equation 2 can be realized by an OTA with BJT differential pair, such as OTAs 220 and 230. The linear conductance in equation 2 can be realized by using a pair of resistors as the load of the differential pair, such as resistors 242 and 244 of load 240. Further, each sensor stage is fully differential (i.e. differential input to differential output) which has a good immunity to common-mode noise. Also, this means that in Eq. 2, $V_i$ stands for the differential voltage output of the i-th stage.

Although the examples of FIGS. 12-13 use bipolar junction transistors (BJT's) with input signals applied to the transistor bases, it is within the contemplation of the present disclosure to use alternate technologies such as field effect transistors (FETs) and more specifically, multi-gate (e.g., dual gate) MOSFETs whose normal bias states (the bias states when a zero magnitude input signal is applied) are controlled to be in respective nonlinear response regions by controlling the bias voltages applied to the second gate of the respective dual or multi-gated devices (or alternatively or additionally to a second source terminal of a multi-gate, multi-sources FET if such is used for establishing electric field in and around the channel regions of such field effect controlled devices). As in the case of controlling the normal bias point of the bipolar transistors, the normal bias providing circuit for the FET version may be a temperature compensated one. It is within the contemplation of the disclosure that the FET-based input sensing stages may be used to detect, not just AC input signals, but also DC input signals.

Having described and illustrated the principles of the present disclosure of invention with reference to described embodiments, it will be recognized that the described embodiments may be modified in arrangement and detail without departing from such principles. While the exemplary embodiments are described and illustrated herein, it will be appreciated that they are merely illustrative.

If any disclosures are incorporated herein by reference and such incorporated disclosures conflict in part or whole with the present disclosure, then to the extent of conflict, and/or broader disclosure, and/or broader definition of terms, the present disclosure controls. If such incorporated disclosures conflict in part or whole with one another, then to the extent of conflict, the later-dated disclosure controls.

Unless expressly stated otherwise herein, ordinary terms have their corresponding ordinary meanings within the respective contexts of their presentations, and ordinary terms of art have their corresponding regular meanings within the relevant technical arts and within the respective contexts of their presentations herein. Descriptions above regarding related technologies are not admissions that the technologies or possible relations between them were appreciated by artisans of ordinary skill in the areas of endeavor to which the present disclosure most closely pertains.

Given the above disclosure of general concepts and specific embodiments, the scope of protection sought is to be defined by the claims appended hereto. The issued claims are not to be taken as limiting Applicant's right to claim disclosed, but not yet literally claimed subject matter by way of one or more further applications including those filed pursuant to 35 U.S.C. §120 and/or 35 U.S.C. §251. A general claim to all here disclosed and inventive matter is hereby made.

What is claimed is:

1. A method of detecting changes in biologically sourced electrical signals, the method comprising:
    coupling, via an electrode, a biologically sourced electrical signal to a meta-stable and hair-trigger wise perturbable system, wherein the meta-stable and hair-trigger wise perturbable system has a first oscillatory mode when the coupled electrical signal has a strength below a first predetermined level and has a distinguishable second oscillatory or non-oscillatory mode when the coupled electrical signal has a strength above the first predetermined level but below a second predetermined level;
    determining whether the coupled electrical signal changes an operating mode of the perturbable system in a distinguishable way; and
    if there is a determined change of operating mode, correlating the determined change to a corresponding and predetermined range of sourced electrical signals that are predetermined to equivalently cause such a determined change.

2. The method of claim 1 wherein the biologically sourced electrical signals are sourced from in vivo nerve cells.

3. The method of claim 2 wherein the biologically sourced electrical signals are sourced from intra-cranial nerve cells.

4. The method of claim 1 wherein the coupling of the biologically sourced electrical signals includes transmitting them through respective DC blocking capacitances.

5. The method of claim 1 wherein the meta-stable and hair-trigger wise perturbable system has a distinguishable third oscillatory mode when the coupled electrical signal has a strength above the second predetermined level.

6. The method of claim 1 wherein the coupling of the biologically sourced electrical signals includes transmitting a first such biologically sourced signal as a first differential signal pair and transmitting a second such biologically sourced signal as a reference signal.

7. The method of claim 6 wherein the reference signal is coupled to the perturbable system by way of a relatively short conductor and the first differential signal pair is coupled to the perturbable system by way of a corresponding first pair of longer conductors.

8. The method of claim 7 wherein the reference signal is obtained from a corresponding reference electrode and the perturbable system is packaged in a housing that is affixed to or integrally formed as including the reference electrode.

9. The method of claim 1 and further comprising:
   wirelessly transmitting a telemetry signal representing a determined change of the perturbable system or a corresponding and predetermined range of sourced electrical signals corresponding to the determined change from a first housing that houses the perturbable system to a second housing that houses a downstream signal or data processing system that is configured to further process the wirelessly transmitted telemetry signal.

\* \* \* \* \*